(12) United States Patent
Akiba

(10) Patent No.: US 6,497,652 B2
(45) Date of Patent: Dec. 24, 2002

(54) LINEAR TRANSMISSION MEMBER DRIVING UNIT FOR ENDOSCOPE WITH ROTATION STOPPER MECHANISM

(75) Inventor: Haruo Akiba, Saitama (JP)

(73) Assignee: Fuji Photo Optical Co., Ltd., Saitama (JP)

(*) Notice: Subject to any disclaimer, the term of this patent is extended or adjusted under 35 U.S.C. 154(b) by 3 days.

(21) Appl. No.: 09/903,605

(22) Filed: Jul. 13, 2001

(65) Prior Publication Data

US 2002/0016526 A1 Feb. 7, 2002

(30) Foreign Application Priority Data

Aug. 1, 2000 (JP) ............................... 2000-232811

(51) Int. Cl.⁷ .................................................. A61B 1/00
(52) U.S. Cl. ........................ 600/167; 600/168; 74/89.39
(58) Field of Search .................................. 600/167, 168, 600/173; 74/25, 89.37, 89.38, 89.39; 359/824

(56) References Cited

U.S. PATENT DOCUMENTS

| | | | | |
|---|---|---|---|---|
| 5,935,057 A | * | 8/1999 | Lichtman et al. | 600/129 |
| 6,371,909 B1 | * | 4/2002 | Hoeg et al. | 600/112 |
| 6,381,903 B1 | * | 5/2002 | Desrochers et al. | 160/310 |
| 6,409,658 B1 | * | 6/2002 | Mitsumori | 600/130 |
| 6,422,995 B2 | * | 7/2002 | Akiba | 600/167 |

OTHER PUBLICATIONS

Japanese Patent Office, "Patent Abstracts of Japan", Publication No.: 2000–111806, Publication Date: Apr. 21, 2000, Application No.: 10–283822, Date of Filing: Oct. 6, 1998.

* cited by examiner

Primary Examiner—John P. Leubecker
(74) Attorney, Agent, or Firm—Snider & Associates; Ronald R. Snider

(57) ABSTRACT

A rotary driving member at the tip end portion is rotated by a motor through a linear transmission member, and the rotation of this rotary driving member is converted into a straight-line motion to thereby enable a movable lens for making the observation distance variable to move within a predetermined range. A motor shaft and the linear transmission member are connected to each other by the shaft connecting member, whereby the linear transmission member is constructed so as to be able to move in an axial direction, and on the outer peripheral portion of the shaft connecting member, a rotating member having a protruded portion is mounted, and the rotation stopper mechanism is constituted by the rotating member and a locking pin portion. Thereby, any kink of the linear transmission member is eliminated to improve the response of driving control, and loads given to the tip end portion driving member and the linear transmission member are reduced.

5 Claims, 4 Drawing Sheets

40: LINEAR TRANSMISSION MEMBER
46: PROTRUDEO PORTION
47: RORATING MEMBER
48: LOCKING PIN PORTION

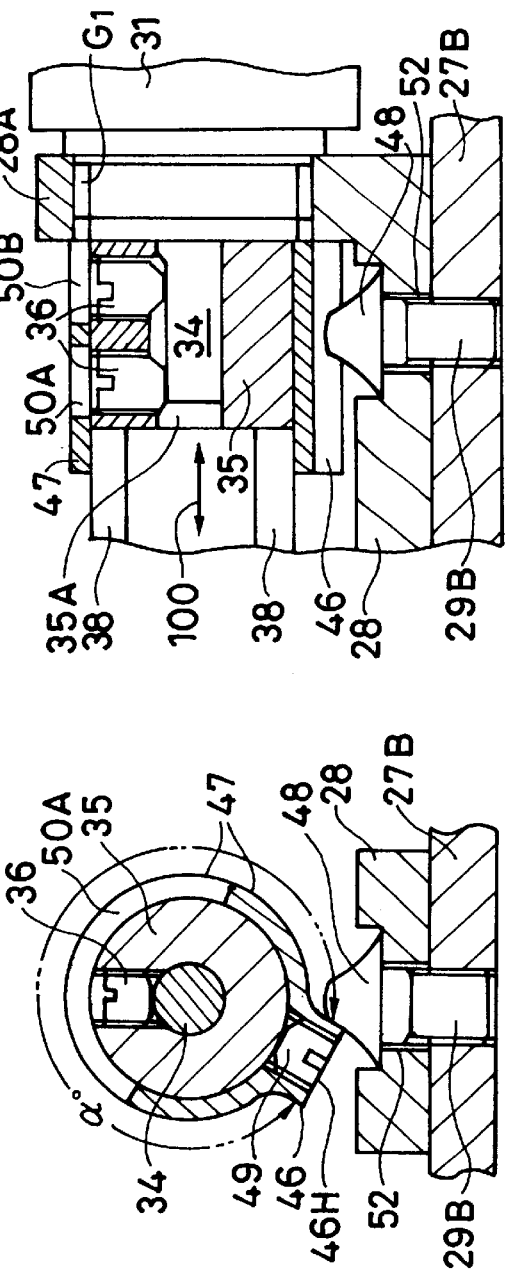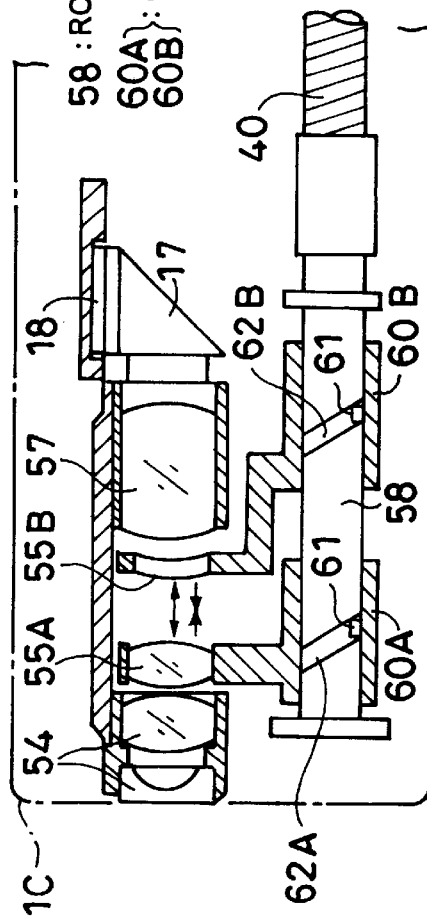

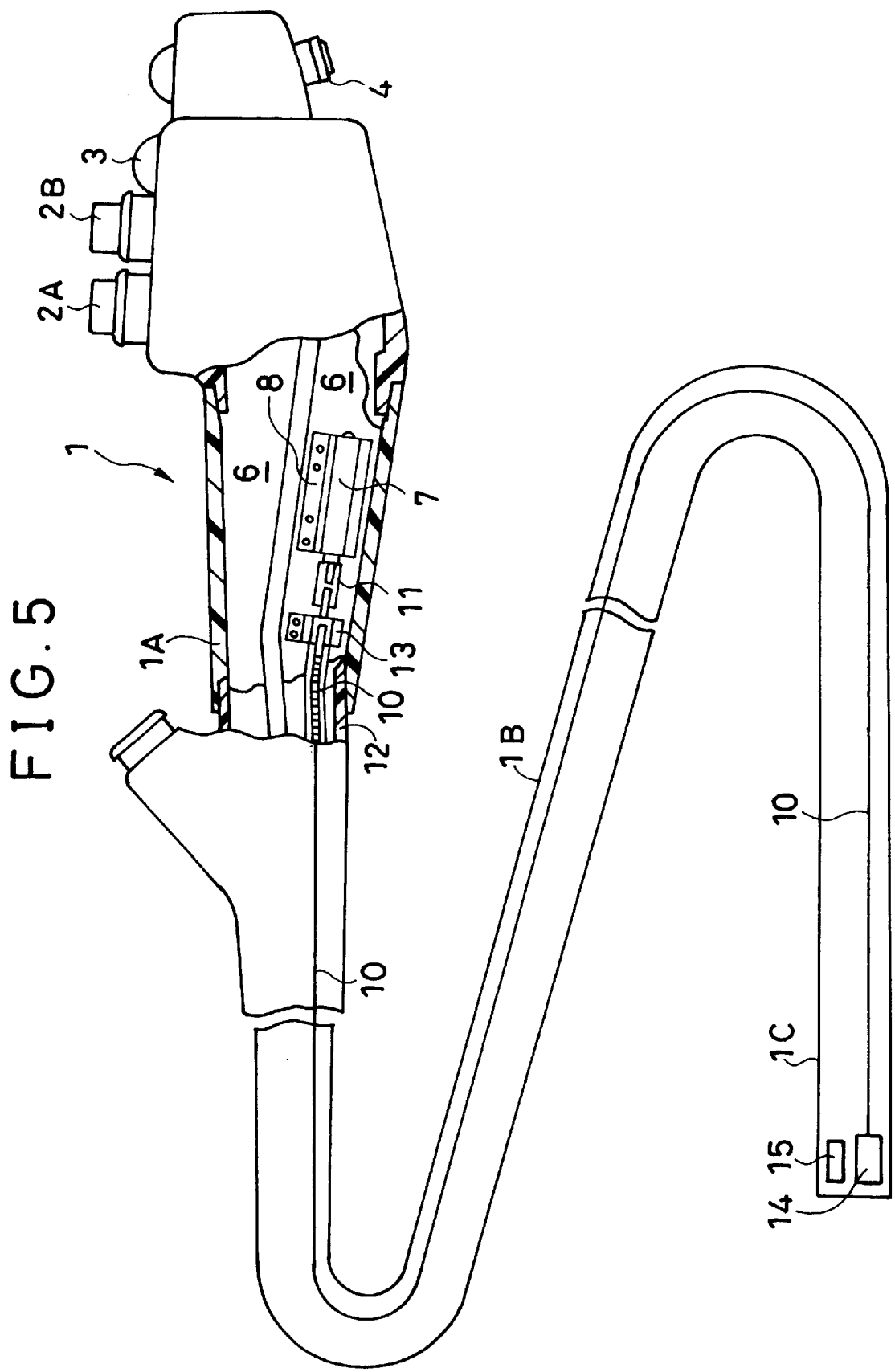

LINEAR TRANSMISSION MEMBER DRIVING UNIT FOR ENDOSCOPE WITH ROTATION STOPPER MECHANISM

BACKGROUND OF THE INVENTION

This application claims the priority of Japanese Patent Application No. 2000-232811 filed on Aug. 1, 2000 which is incorporated herein by reference.

1. Field of the Invention

The present invention relates to a linear transmission member driving unit for an endoscope, and more particularly to a structure of a driving unit for rotating, by a motor, a linear transmission member for changing an observation distance (including changing depth of field).

2. Description of the Prior Art

FIGS. 4 and 5 show a structure (for example, Japanese Patent Laid-Open No. 2000-111806) of an endoscope, to which a mechanism for making an observation distance (or depth of field) variable is applied, and first with reference to FIG. 5, the description will be made of the endoscope as a whole. The endoscope is constituted by an operating unit 1A, an insertion portion 1B having flexibility and a tip end portion 1C, and the operating unit 1A is provided with a air-supply/water-supply operating button 2A, a suction operating button 2B, a freeze switch 3, an observation distance variable switch 4 and the like. This observation distance variable switch 4 is capable of changing a focal length to a far direction or a near direction.

In this operating unit 1A, a motor 7 is mounted on a chassis 6 by means of a holding member 8, and to this motor 7, a linear transmission member 10 consisting of a multiple coiled spring is mounted through a shaft connector 11. This linear transmission member 10 is inserted in a protective tube 12 for preventing any interference with other members, and this protective tube 12 is attached to the chassis 6 by means of the holding member 13. These linear transmission member 10 and protective tube 12 are arranged from the operating unit 1A to the tip end portion IC through the insertion portion 1B.

At this tip end portion 1C, there are provided an objective optical system 14 and a CCD 15, which is a solid state imaging device, and a movable lens installed in this objective optical system 14 for making the observation distance variable is driven by the linear transmission member 10. More specifically, as shown in FIG. 4, at the tip end portion 1C, there are arranged a front-side lens 17, a movable lens 18, and a prism 19, and below the prism 19, a CCD 20 is optically connected. The holding member 22 of the movable lens 18 has a female threaded portion in its top portion, and there is arranged a rotary driving member 23, whose male threaded portion threadedly engages this female threaded portion, and to this rotary driving member 23, the linear transmission member 10 is coupled.

Further, the rotary driving member 23 is provided with a first stopper 25A having a male threaded portion at its end and a second stopper 25B in such a manner that the inside of a wall portion, in which the inside diameter at a rear end of the holding member 22 becomes smaller, abuts on the first stopper 25A, and the outside abuts on the second stopper 25B.

According to such structure, rotation of the motor 7 is transmitted to the rotary driving member 23 at the tip end portion 1C through the linear transmission member 10, and the rotational motion of this rotary driving member 23 is converted into a straight-line motion by means of a combination of threaded engagement with the holding member 22. Thereby, the movable lens 18 moves back and forth within a range D1 (FIG. 4) to be set by the first stopper 25A and the second stopper 25B, and it becomes possible to change the observation distance to be set by the objective optical system.

BRIEF SUMMARY OF THE INVENTION

OBJECT OF THE INVENTION

In the above-described linear transmission member driving unit, however, the linear transmission member 10 consists of a multiple coiled spring, by means of which the operating unit 1A and the tip end portion 1C are coupled over a comparatively long distance therebetween, and therefore, driving control is not linearly performed, but particularly the response at the driving end (terminal end) is not satisfactory. More specifically, in the driving control of the motor 7, the holding member 22 of the movable lens 18 abuts on the first stopper 25A or the second stopper 25B to reach the driving end, and when a load to be given to the rotating shaft of the motor 7 through the linear transmission member 10 exceeds a predetermined value, the motor 7 is controlled to be stopped.

However, since the rotary driving force to be transmitted from the motor 7 is absorbed by the kink of the linear transmission member 10, no stop control is performed in the control circuit before a fixed amount of load is applied to the motor 7 since the movable lens 18 stops at the driving end. Also, even when the direction of rotation is reversed at the driving end, since the movable lens 18 starts to move after the kink of the linear transmission member 10 is completely returned, a time lag occurs between when the observation distance variable switch 4 is operated, and when actually driven, and as a result, the operability is worsened.

Also, in order to move the movable lens 18, a force to be given to the tip end portion driving member is increased by the kink of the linear transmission member 10, and since a miniaturized driving member is used for the tip end portion of the endoscope which has particularly a fine diameter, the durability of the tip end portion driving member is deteriorated. Similarly, there was a problem that the durability of the linear transmission member 10 itself is also deteriorated due to the kink.

As means for avoiding such a problem, it can be conceived to reinforce the linear transmission member 10, and to increase its diameter so as not to cause any kink phenomenon even for the maximum driving force for improving the transmission ability. Even in this case, however, it is possible to reduce the time lag between during operating and during driving to some extent, but sufficient response cannot be obtained. And yet, this observation distance variable operation is structured so as to be able to change the operating speed stepwise, and since the linear transmission member 10 becomes heavier by increasing the diameter, it becomes difficult to execute high-speed operation.

Also, when the diameter of the linear transmission member 10 is increased, the hardness also becomes higher, and therefore, the transmission characteristic of the linear transmission member 10 is deteriorated because of a change in posture of the insertion portion 1B which can be freely bent, and there is also an inconvenience that there occurs a difference in time required for the observation distance variable operation.

The present invention has been achieved in view of the above-described problems, and an object of the present invention is to provide a linear transmission member driving unit for an endoscope capable of obtaining high operability in the function for making the observation distance variable and the like by improving the response of driving control, and improving durability of the tip end portion driving member and the linear transmission member.

SUMMARY OF THE INVENTION

In order to achieve the object, according to the present invention, there is provided a linear transmission member driving unit comprising: a linear transmission member which rotates to drive an object; a motor, to which this linear transmission member is shaft-connected; a guide member for regulating a range of movement of the object driven by the linear transmission member; and a rotation stopper mechanism arranged between the linear transmission member and the motor, for stopping the rotation of the linear transmission member correspondingly to a range of movement of the object regulated by the guide member.

The another invention is characterized in that it is arranged such that rotation of the linear transmission member is transmitted to a lens driving unit, to make a movable lens for performing a predetermined function move back and forth within a predetermined range, and a range of rotation of the linear transmission member set by the rotation stopper mechanism is set to be equal to or more than a range of rotation of linear transmission member required for the lens driving unit to accomplish a predetermined function.

According to the above-described structure, the rotation stopper mechanism is arranged in the vicinity of the motor shaft, and by means of this stopper mechanism, there is secured a little larger range than the range of movement of the movable lens which accomplishes (ensures), for example, the observation distance variable function (scaling function) to stop the rotation of the linear transmission member. As a result, the kink of the linear transmission member is suppressed to a minimum, and the response of the movable lens can be enhanced under the rapid stop control of the motor.

The another invention is characterized in that there is provided a movable shaft coupling mechanism for coupling an end portion of the linear transmission member to a shaft of the motor, and enabling the linear transmission member to move in a motor rotating shaft direction.

According to the above-described structure, since the end portion of the linear transmission member is coupled to the motor shaft by means of the movable shaft coupling mechanism, even if the linear transmission member expands or contracts because of a bending operation or the like of the endoscope insertion portion, that amount corresponding to the expansion and contraction can be absorbed within the coupling mechanism, the load to be applied to the motor rotating shaft can be made substantially constant, and a scaling operation or the like can be performed by a stable rotary driving force.

The another invention is characterized in that the rotation stopper mechanism is constructed of: a rotating member integrally provided on the outer periphery of the shaft connecting member of the movable shaft coupling mechanism and having a protruded portion; and a locking portion for locking a protruded portion of this rotating member, and that the rotating member is arranged in an outer peripheral position of the motor shaft by providing the motor shaft with a notch portion, through which a screw for mounting the shaft connecting member is inserted.

According to the above-described structure, the shaft connecting member is mounted to the motor shaft while a screw is being inserted through the notch portion provided in the rotating member of the rotation stopper mechanism, whereby the stopper mechanism can be arranged at an outer peripheral position of the motor shaft, and a stable stop operation can be obtained. Also, the rotating member can be easily mounted.

The another invention is characterized in that in the rotating member of the rotation stopper mechanism, its protruded portion is formed with a tapped hole, and the rotating member concerned is screwed and fixed to the shaft connecting member through this tapped hole on the protruded portion.

According to the above-described structure, since screwing and fixing are performed through a tapped hole formed in the protruded portion of the rotating member, sufficient strength can be secured for the tightening and fixing, and the range of rotation can be set large through the use of all the portions other than the protruded portion.

BRIEF DESCRIPTION OF THE DRAWINGS

FIG. 2(A) is an enlarged sectional view showing a motor shaft portion in which a rotation stopper mechanism is arranged in the motor driving unit according to the embodiment;

FIG. 2(B) is a sectional view taken on a portion in which the main elements appear showing the motor shaft portion of FIG. 2(A);

FIG. 2(C) is a sectional view showing structure of a lens driving unit at the tip end portion of the endoscope;

FIG. 5 is a conventional partial sectional view showing the overall structure of the endoscope, to which a mechanism for making the observation distance variable is applied.

DETAILED DESCRIPTION OF THE PREFERRED EMBODIMENTS

Figure 1A:
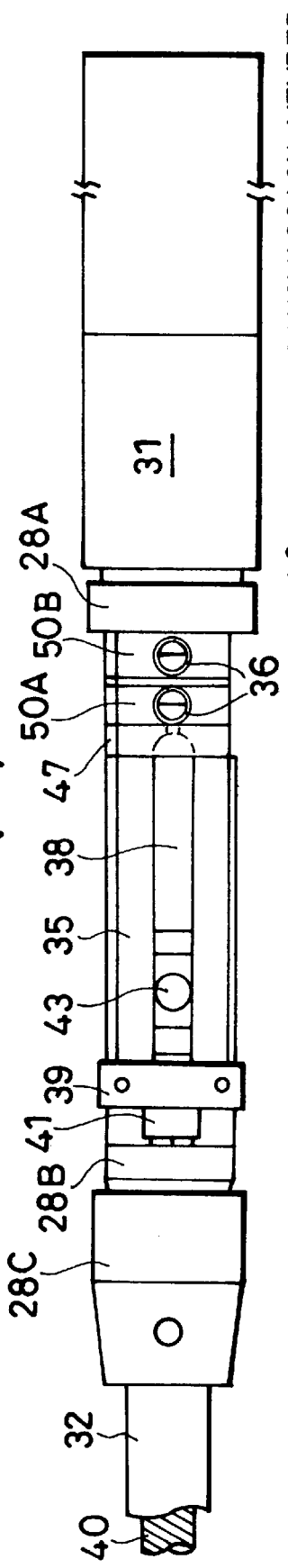
FIG. 1(A) is a top view showing structure of a motor driving unit for a linear transmission member driving unit for an endoscope according to an embodiment of the present invention.

FIGS. 1 to 4 show a linear transmission member driving unit for an endoscope according to the embodiment, and first the description will be made of structure of the motor driving unit side. FIG. 1(A) is a view showing the driving unit of FIG. 1(B) as viewed from above, and FIG. 1(B) is a view showing the driving unit as viewed from the side with the mounting chassis placed horizontally. In FIGS. 1(A) and 1(B), the motor driving unit is provided within the endoscope operating unit (1A of FIG. 5) as it is in the prior art, and on the lower chassis 27B of two sheets of chassis 27A and 27B arranged at the center within this operating unit, the holding member 28 of the driving unit (motor and protective tube) is mounted by means of a plurality of screws, for example, two screw members 29A and 29B.

In this holding member 28, a tip end male screw (threaded portion $G_1$) of the motor 31 threadedly engages the female thread (threaded portion $G_1$) within a ring portion 28A of a rear-side holding portion and is fixed, and a protective tube 32 is held and fixed by means of combined cylindrical members 28B to 28D of the front-side holding portion. In other words, on a contact surface between cylindrical members 28B and 28C, there is formed a threaded portion $G_2$ for combination by threaded engagement, the tip end-side outer periphery of this cylindrical member 28B and the inner periphery of the cylindrical member 28D are made into a tapered-off surface, and between them, there is provided a gap in which the protective tube 32 is interposed. Thus, while interposed between the cylindrical member 28B and the cylindrical member 28D, the cylindrical member 28C threadedly engages the cylindrical member 28B by means of the threaded portion $G_2$, whereby the protective tube 32 is fixed.

On the other hand, as also shown in FIG. 2(A), the shaft 34 of the motor 31 is mounted to a shaft connecting member 35. More specifically, the shaft 34 is inserted into a mounting hole 35A of this shaft connecting member 35, and a D-cut surface of this shaft 34 is fastened by means of two screws 36, whereby the motor shaft 34 is fixed to the shaft connecting member 35. This shaft connecting member 35 has a main body as a cylindrical member, and for example, at two opposite places of this cylindrical member-shaped wall, there are formed sliding guide holes 38 along the rotating shaft direction 100, and at their tip ends, stopper rings 39 are mounted with adhesive or the like.

Also, an end portion of the linear transmission member 40 consisting of a multiple coiled spring or the like arranged within the protective tube 32 is inserted into a sleeve 41 and is fixed by means of soldering or the like, and this sleeve 41 is constructed such that it has ring-shaped protrusions in two front and rear places and slides within the cylindrical member of the shaft connecting member 35. This sleeve 41 is formed with a mounting hole 41A in a direction perpendicular to the rotating shaft direction 100, and a pin 43 is inserted into this mounting hole 41A and is mounted by means of a screw 44. In other words, the tip end of the screw 44 abuts on the conical concave portion of this pin 43, whereby the pin 43 is fixed to the sleeve 41. This pin 43 serves to prevent the linear transmission member 40 from slipping.

In such a movable shaft coupling mechanism for the linear transmission member, there is provided a rotation stopper mechanism on the outer peripheral portion of the motor shaft 34 of the motor 31. This rotation stopper mechanism consists, as shown in FIGS. 2(A) and 2(B), of a cylindrical rotating member 47 formed with a wall-shaped protruded portion 46 along the axial direction on the outer peripheral portion, and a locking pin portion (locking portion) 48 of a pin and screw member 29B mounted onto the lower chassis 27B.

More specifically, as shown in FIG. 2(B), in the protruded portion 46 of the rotating member 47, there are provided tapped holes 46H, for example, at two front and rear places, and screws 49 are inserted into these tapped holes 46H and the rotating member 47 is mounted to the shaft connecting member 35. Also, this rotating member 47 is, as shown, formed with notch portions 50A and 50B at two places correspondingly to positions of mounting screws 36 of the shaft connecting member 35. These notch portions 50A and 50B are provided with a little larger width than the diameter of the screw 36 and a size of about 180° in the circumferential direction.

Further, the pin and screw member 29B serves as a screw for fixing the holding member 28 to the chassis 27B and a locking portion for the stopper mechanism, and is constructed such that the lower side serves as the threaded portion, and at its head portion, an umbrella-shaped locking pin portion 48 is formed. This pin and screw member 29B is, as shown in FIGS. 2(A) and 2(B), secured to the chassis 27B by screws through the engaging hole 52 of the holding member 28, whereby the holding member 28 is fixed, and on the other hand, the protruded portion 46 of the rotating member 47 is restrained by the locking pin portion 48. According to this rotation stopper function, in a state in which an angle α [FIG. 2(B)] to be set by width of the protruded portion 46 of the rotating member 47, for example, a rotating range of 310° has been secured, the rotation can be stopped at both ends (near end and far end) of the shaft connecting member 35.

Figure 1B:
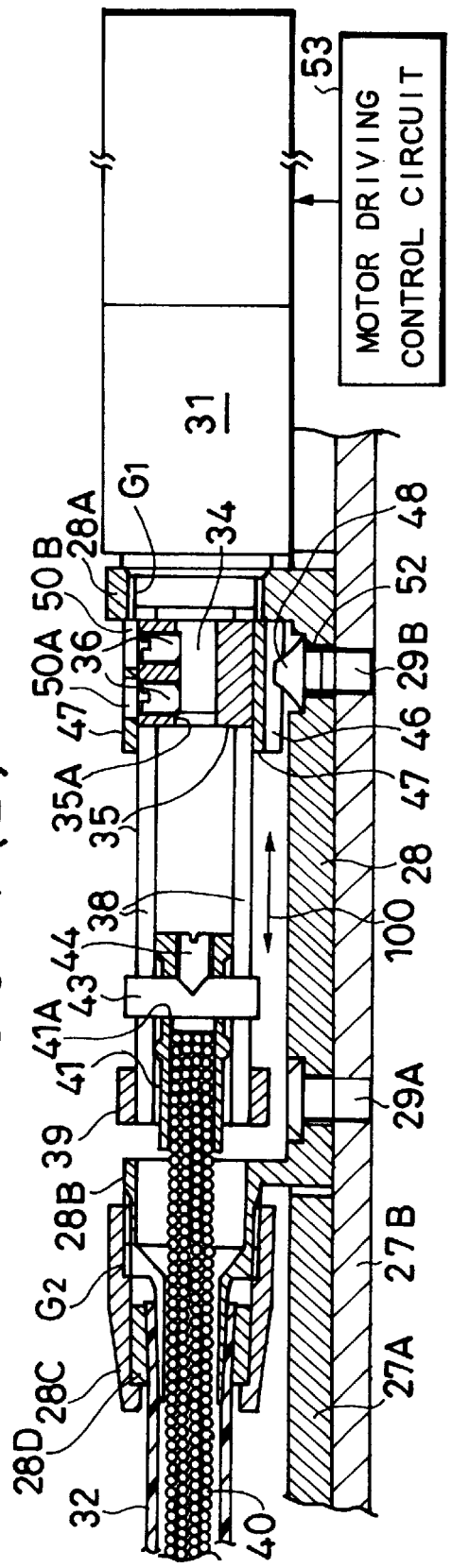
FIG. 1(B) is a partially exploded side view showing the motor driving unit of FIG. 1(A)

Also, as shown in FIG. 1(B), in order to rotationally control the motor 31, a motor driving control circuit 53 is provided within the operating unit (1A of FIG. 5) or the like, and this motor driving control circuit 53 rotationally (forward rotation or reverse rotation) controls the motor 31 at predetermined plural speeds by operating (operating in the far direction or in the near direction) the observation distance variable switch (4 of FIG. 5, seesaw switch or the like), and when a load exceeding a predetermined value is applied to the motor shaft 34, controls the motor 31 to stop it.

FIG. 2(C) shows the structure of the lens driving unit side within the tip end portion 1C, at this tip end portion 1C, there is provided an objective optical system consisting of a front-side lens (or group) 54, two movable lenses (or group) 55A and 55B for changing the observation distance and a rear-side lens (or group) 57, and to this objective optical system, a CCD 18 is optically connected through a prism 17. At the holding member for the movable lenses 55A and 55B, there are integrally provided cylindrical portions 60A and 60B, each having a through-hole, through which a rotary driving member 58 coupled to the linear transmission member 40 is inserted. On the inner walls of the through-holes of these cylindrical portions 60A and 60B, there are provided pins 61, at the outer periphery of the other rotary driving member 58, there are formed cam grooves 62A and 62B for engaging the pins 61, and this rotary driving member 58 and the cylindrical portions 60A and 60B function as a guide member.

Figure 3:
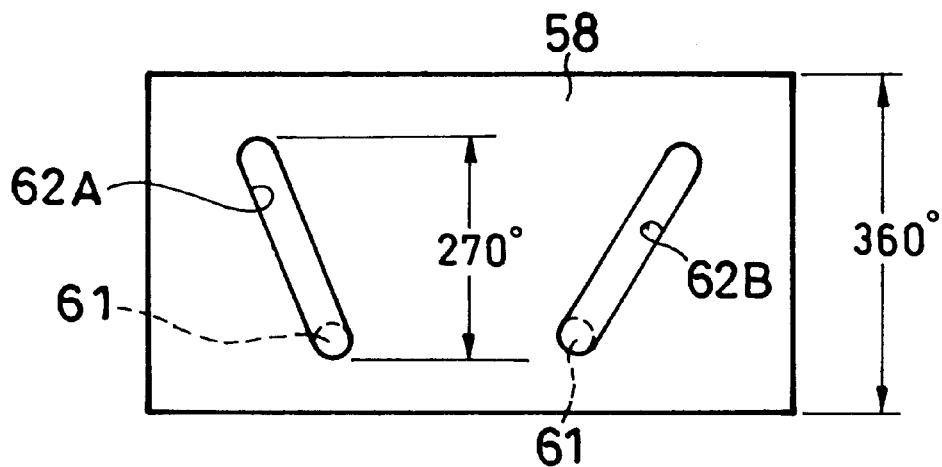
FIG. 3 is a view showing a rotary driving member to be arranged in a lens driving unit according to the embodiment, developed such that its cam groove appears.
Figure 4:
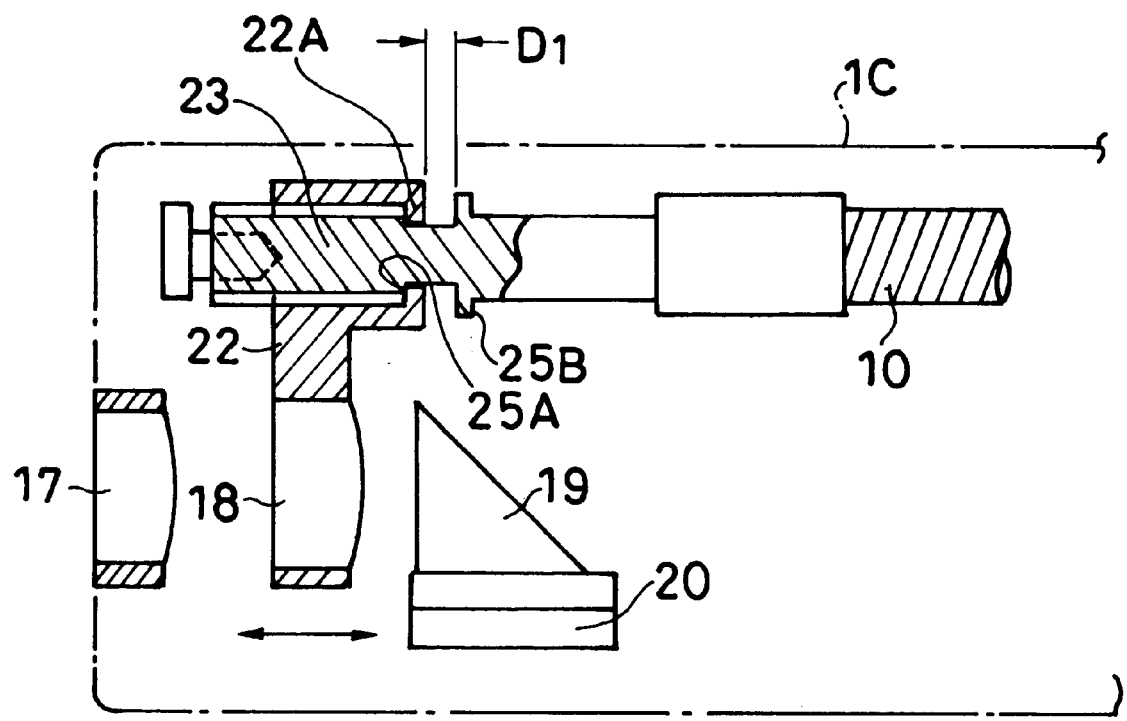
FIG. 4 is a conventional partial sectional view showing structure of a lens driving unit at the tip end of the endoscope, to which a mechanism for making the observation distance variable is applied.

FIG. 3 shows a development for explaining the cam grooves 62A and 62B of the rotary driving member 58, and in the example concerned, the cam grooves 62A and 62B are provided with a range of 270° as shown. According to such structure of the guide member, the rotary driving member 58 rotates within the range of 270° by means of the linear transmission member 40, and the movable lenses 55A and 55B are caused to linearly move back and forth in the optical axis direction in a direction (direction to approach to each other or retract) and in an amount corresponding to respective inclinations of the cam grooves 62A and 62B of this rotary driving member 58.

The embodiment has the above-described structure, and when first the motor driving control circuit 53 of FIG. 1(B) drives the motor 31 based on an operation of the observation distance variable switch, rotation of the motor shaft 34 is transmitted to the rotary driving member 58 of FIG. 1(C) through the shaft connecting member 35 and the linear transmission member 40. Then, as described above, the rotation of the rotary driving member 58 is converted into a straight-line motion by the engagement between its cam groove 62A, 62B and the pin 61 of the cylindrical member 60A, 60B, and the movable lenses 55A, 55B move so as to approach to each other or retract in the optical axis direction for scaling operation.

Thus, when the pins 61 abut on both end portions of the cam groove 62A and 62B, the movement of the movable lens 55A and 55B is stopped, but since no stop command is given to the motor 31 at this point of time, the linear transmission member 40 is further going to rotate in the same direction. Conventionally, the operation of the motor has not been stopped before a fixed amount or more load is given to the motor shaft 34 by a considerable amount of kink of this linear transmission member 40, but the response has been degraded. According to the present invention, the kink of the linear transmission member 40 causing the response to be degraded will be restrained by the rotation stopper mechanism.

More specifically, when the moving range of the cam grooves 62A and 62B is assumed to be an angle of 270° and a rotation regulating range by the rotation stopper mechanism is assumed to be an angle of 310° as described above, a protruded portion 46 of a rotator 47 provided for the shaft connecting member 35 on the motor driving unit side bumps against a locking pin portion 48 at a point of time whereat the cam grooves 62A and 62B rotate by about 20° [(310°−270°)÷2=20°] since the pin 61 abuts on the end portion of the cam groove 62A, 62B. At this point of time, the motor driving control circuit 53 detects a load equal to or more than a predetermined value to stop the motor 31.

Accordingly, in the example concerned, the motor 31 is stopped before the linear transmission member 40 is twisted, the response of driving is improved to improve the operability of making the observation distance variable. Also, loads to be applied to the lens holding members 60A and 60B having the pin 61 arranged at the tip end portion (1C), the driving unit for the rotary driving member 58 having the cam grooves 62A and 62B, and the like, and the linear transmission member 40 are more reduced than in the conventional cases, and the durability of the driving member can be improved.

Further, in the example concerned, the linear transmission member 40 and the motor shaft 34 are coupled to each other by means of the movable shaft coupling mechanism, and the description will be simply made of the operation of the movable shaft coupling mechanism. In FIGS. 1(A), (B), the sleeve 41 holding the end portion of the linear transmission member 40 moves in the rotating shaft direction 100 within the shaft connecting member 35 within a range in which the pin 43 slides within a sliding guide hole 38. On the other hand, the linear transmission member 40 and the sleeve 41 are fixed to the shaft connecting member 35 in the rotating direction by means of engagement between the sliding guide hole 38 and the pin 43, and the rotation of the motor 31 is transmitted to the linear transmission member 40 through the motor shaft 34 and the shaft connecting member 35.

Therefore, even if the linear transmission member 40 expands and contracts by a bending operation or the like of the endoscope insertion portion 1B, that amount corresponding to the expansion and contraction can be absorbed within the movable coupling mechanism, the load to be applied to the motor shaft 34 can be made substantially constant during an operation of any other than the driving end, and the scaling operation or the like can be performed by a stable rotary driving force.

Also, in the shaft connecting member 35 of the movable shaft connecting mechanism according to the example concerned, the structure is arranged such that the shaft connecting member 35 is mounted close to the motor shaft 34 while a screw 36 is being inserted through notch portions 50A and 50B provided for the rotating member 47 of the rotation stopper mechanism, whereby there is an advantage that the rotation stopper mechanism is arranged at an outer peripheral position of the motor shaft 34 (a load caused by stoppage is directly and effectively given to the motor shaft) to obtain a stable stop operation. In this respect, this rotation stopper mechanism can be arranged at any place as long as it is an outer peripheral position of the shaft connecting member 35, and another structure can be adopted.

Further, the rotating member 47 is fastened and fixed by a screw 49 through a tapped hole 46H formed in its protruded portion 46, and the protruded portion 46 having a heavy wall thickness is used for the fixation, and therefore, there are advantages that a sufficient strength can be secured in the fixation, and that all the portions other than the protruded portion 46 can be used as the range of rotation. In this respect, this protruded portion 46 may not be provided in the rotating member 47, but be directly integrally formed with the shaft connecting member 35.

Also, a regulating angle a to be set by the rotation stopper mechanism according to the embodiment has been set to 310° correspondingly to an angle of the rotary driving member 58 being 270°, but can be set to slightly larger value than the angle of the rotary driving member 58 required to realize the function of making the observation distance variable.

As described above, according to the present invention, the rotary driving force of the motor is transmitted to the lens driving unit at the tip end portion through the linear transmission member, in an endoscope for driving a movable lens for changing, for example, the observation distance, there is provided a rotation stopper mechanism for stopping the rotation of the linear transmission member correspondingly to the moving distance of the movable lens between the linear transmission member concerned and the motor. Therefore, the response of the driving control is improved by eliminating the kink of the linear transmission member, and high operability can be obtained in the function of making the observation distance variable and the like. Moreover, since the load at the driving end is reduced, it becomes possible to improve the durability of the driving member at the tip end portion and the linear transmission member.

Also, since the linear transmission member is not made heavier by increasing the diameter, but a high-speed operation for making the observation distance variable can be more easily executed, and further the hardness of the linear transmission member can be also made lower, when the posture of the endoscope insertion portion changes, the transmission characteristic of the linear transmission member is prevented for being deteriorated to cause a difference in time required for the operation for making observation distance variable.

Further, through the use of the movable shaft coupling mechanism, the linear transmission member advances or retreats in the rotating shaft direction in response to an angle bending operation so that it itself does not expand nor contract any longer. Also, in the operations of any other than the driving end, the load to the motor shaft becomes constant, and a stable operation such as, for example, scaling speed and the like can be obtained even if the posture of the endoscope insertion portion changes.

Also, since the shaft connecting member is mounted close to the motor shaft while screws are being inserted through notch portions provided for the rotating member of the rotation stopper mechanism, there is an advantage that a stable stop motion can be obtained. Also, it becomes easier to mount the rotating member of the stopper mechanism.

Further, since screwing and fixing are performed through the tapped hole formed in the protruded portion of the rotating member, there are advantages that a sufficient strength can be secured for fastening and fixing, and that all the portions other than the protruded portion are utilized whereby the range of rotation can be set large.

What is claimed is:

1. A linear transmission member driving unit for an endoscope comprising:

a linear transmission member which rotates to drive an object;

a motor, to which the linear transmission member is shaft-connected;

a guide member for regulating a range of movement of said object driven by said linear transmission member; and a rotation stopper mechanism arranged between said linear transmission member and said motor, for stopping rotation of said linear transmission member correspondingly to a range of movement of said object regulated by said guide member.

2. The linear transmission member driving unit for an endoscope according to claim 1, wherein said object is a lens driving unit for making a movable lens for performing a predetermined function move back and forth within a predetermined range, and a range of rotation of said linear transmission member set by said rotation stopper mechanism is set to be equal to or more than a range of rotation of said linear transmission member required for said lens driving unit to accomplish a predetermined function.

3. The linear transmission member driving unit for an endoscope according to claim 1, wherein there is provided a movable shaft coupling mechanism for coupling an end portion of said linear transmission member to a shaft of said motor, and enabling said linear transmission member to move in a motor rotating shaft direction.

4. The linear transmission member driving unit for an endoscope according to claim 3, wherein said rotation stopper mechanism is constructed of: a rotating member integrally provided on the outer periphery of a shaft connecting member of said movable shaft coupling mechanism and having a protruded portion; and a locking portion for locking a protruded portion of said rotating member, and said rotating member is arranged in an outer peripheral position of said motor shaft by providing said motor shaft with a notch portion, through which a screw for mounting said shaft connecting member is inserted.

5. The linear transmission member driving unit for an endoscope according to claim 4, wherein in said rotating member of said rotation stopper mechanism, its protruded portion is formed with a tapped hole, and said rotating member is screwed and fixed to said shaft connecting member through said tapped hole of said protruded portion.

* * * * *